(12) United States Patent
Green et al.

(10) Patent No.: US 10,865,223 B2
(45) Date of Patent: Dec. 15, 2020

(54) PRODUCTION OF PULSE PROTEIN PRODUCT

(71) Applicants: Brent E. Green, Warren (CA); Martin Schweizer, Winnipeg (CA); Sampson Russ, Oakville (CA)

(72) Inventors: Brent E. Green, Warren (CA); Martin Schweizer, Winnipeg (CA); Sampson Russ, Oakville (CA)

(73) Assignee: BURCON NUTRASCIENCE (MB) CORP., Winnepeg (CA)

( * ) Notice: Subject to any disclaimer, the term of this patent is extended or adjusted under 35 U.S.C. 154(b) by 0 days.

(21) Appl. No.: 14/203,700

(22) Filed: Mar. 11, 2014

(65) Prior Publication Data

US 2014/0256914 A1  Sep. 11, 2014

Related U.S. Application Data

(60) Provisional application No. 61/775,824, filed on Mar. 11, 2013.

(51) Int. Cl.
| | | |
|---|---|---|
| *C07K 1/14* | (2006.01) | |
| *C07K 14/415* | (2006.01) | |
| *A23J 1/14* | (2006.01) | |
| *B01D 11/02* | (2006.01) | |

(52) U.S. Cl.
CPC .......... *C07K 1/145* (2013.01); *A23J 1/14* (2013.01); *B01D 11/02* (2013.01); *C07K 14/415* (2013.01)

(58) Field of Classification Search
CPC .................................. B01D 11/02; A23J 1/14
See application file for complete search history.

(56) References Cited

U.S. PATENT DOCUMENTS

| | | | | |
|---|---|---|---|---|
| 2005/0255226 A1* | 11/2005 | Schweizer | ................ | A23J 1/14 426/656 |
| 2011/0274797 A1* | 11/2011 | Segall | ....................... | A23J 1/14 426/253 |
| 2012/0302735 A1* | 11/2012 | Green | .................. | C07K 14/415 530/378 |

OTHER PUBLICATIONS

Han, "Removal of Phytic Acid from Soybean and Cottonseed Meals"—J. Agric. Food Chem., 1988, 36, pp. 1181-1183.*

* cited by examiner

*Primary Examiner* — Elizabeth Gwartney
(74) *Attorney, Agent, or Firm* — Michael I. Stewart; Marks & Clerk Canada

(57) ABSTRACT

A pulse protein product having a protein content of at least about 50 wt % (N×6.25) d.b. is recovered in the processing of pulse protein source material to form pulse protein products wherein the pulse protein source is extracted in one embodiment with calcium salt solution. The resulting pulse protein solution is separated from the bulk of the residual pulse protein source and then the pulse protein solution is processed to remove finer residual solids, which are optionally washed and then dried to provide the pulse protein product. In another embodiment, the pulse protein source is extracted with water, the bulk of the residual protein source removed and the resulting pulse protein solution treated with calcium salt to precipitate phytic acid. The precipitated phytic acid and any finer residual solids remaining in solution after the initial separation step are removed from the pulse protein solution then optionally washed and dried to provide the pulse protein product.

15 Claims, No Drawings

PRODUCTION OF PULSE PROTEIN PRODUCT

FIELD OF INVENTION

The present invention relates to the production of pulse protein product, preferably pulse protein concentrate.

BACKGROUND TO THE INVENTION

In U.S. patent application Ser. No. 13/103,528 filed May 9, 2011 (US Patent Publication No. 2011-027497 published Nov. 10, 2011), Ser. No. 13/289,264 filed Nov. 4, 2011 (US Patent Publication No. 2012-0135117, published May 31, 2012) and Ser. No. 13/556,357 filed Jul. 24, 2012 (US Patent Publication No. 2013-0189408 published Jul. 25, 2013), assigned to the assignee hereof and the disclosures of which are incorporated herein by reference, there is described the provision of a novel pulse protein product having a protein content of at least about 60 wt % (N×6.25) on a dry weight basis, preferably a pulse protein isolate having a protein content of at least about 90 wt % (N×6.25) d.b. The pulse protein product has a unique combination of properties, namely:
   completely soluble in aqueous media at acid pH values of less than about 4.4
   heat stable in aqueous media at acid pH values of less than about 4.4
   does not require stabilizers or other additives to maintain the protein product in solution
   is low in phytic acid
   requires no enzymes in the production thereof
This novel pulse protein product is prepared by a method which comprises:
   (a) extracting a pulse protein source with an aqueous calcium salt solution, preferably an aqueous calcium chloride solution, to cause solubilization of pulse protein from the protein source and to form an aqueous pulse protein solution,
   (b) separating the aqueous pulse protein solution from residual pulse protein source,
   (c) optionally diluting the aqueous pulse protein solution,
   (d) adjusting the pH of the aqueous pulse protein solution to a pH of about 1.5 to about 4.4, preferably about 2 to about 4, to produce an acidified pulse protein solution,
   (e) optionally clarifying the acidified pulse protein solution if it is not already clear,
   (f) alternatively from steps (b) to (e), optionally, diluting and then adjusting the pH of the combined aqueous pulse protein solution and residual pulse protein source to a pH of about 1.5 to about 4.4, preferably about 2 to about 4, then separating the acidified, preferably clear, pulse protein solution from residual pulse protein source,
   (g) optionally concentrating the aqueous pulse protein solution while maintaining the ionic strength substantially constant by a selective membrane technique,
   (h) optionally diafiltering the optionally concentrated pulse protein solution, and
   (i) optionally drying the optionally concentrated and optionally diafiltered pulse protein solution.
The pulse protein product preferably is an isolate having a protein content of at least about 90 wt %, preferably at least about 100 wt % (N×6.25) d.b.

One of the key steps in producing the novel pulse protein product discussed above is clarification of the aqueous pulse protein solution formed in the extraction step. In general, a decanter centrifuge may be used to remove the bulk of the spent pulse protein source from the aqueous pulse protein solution. A disc stack centrifuge may be employed to remove finer solids not removed by the decanter centrifuge. In general, the solids recovered in the disc stack centrifuge may be combined with solids material discharged from the decanter centrifuge and the combined solids re-extracted to recover additional protein, dried and sold for lower value food or animal feed use, or simply discarded as waste.

SUMMARY OF THE INVENTION

It has now been found that the finer solid material collected by the disc stack centrifuge may be optionally washed to remove impurities and dried to provide a pulse protein product having a protein content of at least about 50 wt %, preferably at least about 60 wt % (N×6.25) d.b., more preferably a pulse protein concentrate having a protein content of at least about 65 wt % (N×6.25) d.b., which may be used in a variety of applications of protein products including but not limited to protein fortification of processed foods and beverages such as nutrition bars. The pulse protein products may also be used in nutritional supplements. Other uses of the pulse protein products are in pet foods, animal feed and in industrial and cosmetic applications and in personal care products.

Accordingly, in one aspect of the present invention, there is provided a method of forming a pulse protein product having a protein content of at least about 50 wt % (N×6.25) d.b., which comprises:
   (a) extracting a pulse protein source with an aqueous calcium salt solution to cause solubilization of pulse protein from the protein source and to form an aqueous pulse protein solution,
   (b) separating the aqueous pulse protein solution from the bulk of the residual pulse protein source,
   (c) applying a second separation step to the pulse protein solution to recover finer residual solids not removed in the initial separation step,
   (d) alternatively from steps (b) to (c), optionally diluting and then adjusting the pH of the combined aqueous pulse protein solution and residual pulse protein source to a pH of about 1.5 to about 4.4, preferably about 2 to about 4, then separating the acidified aqueous pulse protein solution from the bulk of the residual pulse protein source and applying a second separation step to the acidified pulse protein solution to recover finer solids not removed in the initial separation step.
   (e) optionally washing the finer solids to remove impurities, and
   (f) optionally drying the optionally washed finer solids recovered in the second separation step to provide the pulse protein product.

In another aspect of the present invention, there is provided a method of forming a pulse protein product having a protein content of at least about 50 wt % (N×6.25) d.b., which comprises:
   (a) mixing a pulse protein source with water to form a slurry,
   (b) separating the aqueous pulse protein solution from the bulk of the other components of the slurry,
   (c) adding a calcium salt to the aqueous pulse protein solution to precipitate calcium phytate,
   (d) applying a second separation step to the calcium treated pulse protein solution to recover the precipitate as well as any finer solids not removed in the initial separation step (b), (e) alternatively from step (d), optionally diluting and then adjusting the pH of the calcium treated pulse protein solution to a pH of about 1.5 to about 4.4, preferably about 2 to about 4, then applying a second separation step to the acidified calcium treated pulse protein solution to recover the precipitate as well as any finer solids not removed in the initial separation step (b), (f) optionally washing the solid materials recovered in the second separation step to remove impurities, and (g) optionally drying the optionally washed solids recovered in the second separation step.

In each of these embodiments, the solids may be washed with water having a natural pH or with acidified water to remove impurities from the product. Use of acidified water reduces the phytic acid concentration of the product.

The pulse protein product produced by the methods described herein are novel pulse protein products. Accordingly, in another aspect of the present invention, there is provided a pulse protein product having a protein content of at least about 50 wt % (N×6.25) d.b. and at least one parameter selected from the group consisting of:

(a) a phytic acid content of at least 2.5 wt % d.b.,
(b) a crude fibre content of less than about 1.5 wt % d.b.,
(c) a solubility of less than about 15 wt % over a pH range of about 3 to about 6 when solubility is determined by the protein method described in Example 5,
(d) a solubility of less than about 25 wt % over a pH range of about 3 to about 6 when solubility is determined by the pellet method described in Example 5,
(e) a water binding capacity of less than about 2.5 ml/g, and
(f) an oil binding capacity of less than about 2 ml/g.

GENERAL DESCRIPTION OF INVENTION

The initial step of the process of providing the pulse protein product in the above-noted patent applications and utilized herein involves solubilizing pulse protein from a pulse protein source. The pulses to which the invention may be applied include, but are not limited to, lentils, chickpeas, dry peas and dry beans. The pulse protein source may be pulses or any pulse product or by-product derived from the processing of pulses. For example, the pulse protein source may be a flour prepared by grinding an optionally dehulled pulse. As another example, the pulse protein source may be a protein-rich pulse fraction formed by dehulling and grinding a pulse and then air classifying the dehulled and ground material into starch-rich and protein-rich fractions. The pulse protein product recovered from the pulse protein source may be the protein naturally occurring in pulses or the proteinaceous material may be a protein modified by genetic manipulation but possessing characteristic hydrophobic and polar properties of the natural protein.

(a) First Aspect of the Invention:

In this aspect of the invention, protein solubilization from the pulse protein source material is effected most conveniently using calcium chloride solution, although solutions of other calcium salts may be used. In addition, other alkaline earth metal compounds may be used, such as magnesium salts. Further, extraction of the pulse protein from the pulse protein source may be effected using a calcium salt solution in combination with another salt solution, such as sodium chloride. Additionally, in embodiments of the invention, extraction of the pulse protein from the pulse protein source may be effected using water or other salt solution, such as sodium chloride, with calcium salt subsequently being added to the aqueous pulse protein solution produced in the extraction step to precipitate calcium phytate.

As the concentration of the calcium salt solution increases, the degree of solubilization of protein from the pulse protein source initially increases until a maximum value is achieved. Any subsequent increase in salt concentration does not increase the total protein solubilized. The concentration of calcium salt solution which causes maximum protein solubilization varies depending on the salt concerned. It is usually preferred to utilize a concentration value less than about 1.0 M, and more preferably a value of about 0.10 to about 0.15 M.

In a batch process, the salt solubilization of the protein is effected at a temperature of from about 1° C. to about 100° C., preferably about 15° C. to about 65° C., more preferably about 20° C. to about 35° C., preferably accompanied by agitation to decrease the solubilization time, which is usually about 1 to about 60 minutes. It is preferred to effect the solubilization to extract substantially as much protein from the pulse protein source as is practicable, so as to provide an overall high product yield.

In a continuous process, the extraction of the pulse protein from the pulse protein source is carried out in any manner consistent with effecting a continuous extraction of pulse protein from the pulse protein source. In one embodiment, the pulse protein source is continuously mixed with the calcium salt solution and the mixture is conveyed through a pipe or conduit having a length and at a flow rate for a residence time sufficient to effect the desired extraction in accordance with the parameters described herein. In such a continuous procedure, the salt solubilization step is effected, in a time of about 1 minute to about 60 minutes, preferably to effect solubilization to extract substantially as much protein from the pulse protein source as is practicable. The solubilization in the continuous procedure is effected at temperatures between about 1° C. and about 100° C., preferably about 15° C. to about 65° C., more preferably between about 20° C. and about 35° C.

The extraction is generally conducted at a pH of about 4.5 to about 11, preferably about 5 to about 7. The pH of the extraction system (pulse protein source and calcium salt solution) may be adjusted to any desired value within the range of about 4.5 to about 11 for use in the extraction step by the use of any convenient food grade acid, usually hydrochloric acid or phosphoric acid, or food grade alkali, usually sodium hydroxide, as required.

The concentration of pulse protein source in the calcium salt solution during the solubilization step may vary widely. Typical concentration values are about 5 to about 15% w/v.

The protein extraction step with the aqueous salt solution has the additional effect of solubilizing fats which may be present in the pulse protein source, which then results in the fats being present in the aqueous phase.

The protein solution resulting from the extraction step generally has a protein concentration of about 5 to about 50 g/L, preferably about 10 to about 50 g/L.

The aqueous calcium salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of any phenolics in the protein solution.

The aqueous calcium salt solution may contain an anti-foamer, such as any suitable food-grade, non-silicone based anti-foamer, to reduce the volume of foam formed upon further processing. The quantity of anti-foamer employed is generally greater than about 0.0003% w/v.

The aqueous phase resulting from the extraction step then may be separated from the residual pulse protein source, in any convenient manner, such as by employing a decanter centrifuge or any suitable sieve to remove the bulk of the residual pulse protein source, followed by disc centrifugation to remove the finer residual pulse protein source material not removed in the initial separation step. The separation steps may be conducted at any temperature within the range of about 1° to about 100° C., preferably about 15° to about 65° C., more preferably about 20° to about 35° C.

Alternatively, the mixture of aqueous pulse protein solution and residual pulse protein source may be diluted with about 0.1 to about 10 volumes, preferably about 0.5 to about 2 volumes of aqueous diluent. Such dilution is usually effected using water, although dilute salt solution, such as sodium chloride or calcium chloride, having a conductivity up to about 3 mS, may be used. The optionally diluted mixture then is adjusted in pH to a value of about 1.5 to about 4.4, preferably about 2 to about 4, by the addition of any suitable food grade acid, such as hydrochloric acid or phosphoric acid. The acidified aqueous pulse protein solution then may be separated from the residual pulse protein source, in any convenient manner, such as by employing a decanter centrifuge or any suitable sieve to remove the bulk of the residual pulse protein source, followed by disc centrifugation to remove the finer residual pulse protein source material not removed in the initial separation step. The separation steps may be conducted at any temperature within the range of about 1° to about 100° C., preferably about 15° to about 65° C., more preferably about 20° to about 35° C.

The separated finer residual pulse protein source may be washed to remove contaminants as described below.

(b) Second Aspect of the Invention:

In this aspect of the present invention, extraction of the pulse protein from the pulse protein source material is effected using water. In a batch process, the pulse protein source is combined with water, preferably with agitation, for about 1 to about 60 minutes at a temperature of about 1° to about 70° C., preferably about 15° to about 65° C., more preferably about 20° to about 35° C. Temperatures greater than 70° C., such as up to about 100° C. may also be employed provided that the concentration of pulse protein source utilized and the starch content of said pulse protein source are such that the viscosity of the sample does not become prohibitive. It is preferred to effect this mixing step to extract substantially as much protein from the pulse protein source as is practicable, so as to provide an overall high product yield.

In a continuous process, the extraction of the pulse protein from the pulse protein source is carried out in any manner consistent with effecting a continuous extraction of pulse protein from the pulse protein source. In one embodiment, the pulse protein source is continuously mixed with water and the mixture is conveyed through a pipe or conduit having a length and at a flow rate for a residence time sufficient to effect the desired extraction in accordance with the parameters described herein. In such a continuous procedure, the mixing time is about 1 minute to about 60 minutes, preferably to extract substantially as much protein from the pulse protein source as is practicable. The solubilization in the continuous procedure is effected at temperatures from about 1° to about 70° C., preferably about 15° to about 65° C., more preferably about 20° to about 35° C. Temperatures greater than 70° C., such as up to about 100° C. may also be employed provided that the concentration of pulse protein source utilized and the starch content of said pulse protein source are such that the viscosity of the sample does not become prohibitive.

The extraction is generally conducted at a pH of about 4.5 to about 11, preferably about 5 to about 7. The pH of the extraction system (pulse protein source and water) may be adjusted to any desired value within the range of about 4.5 to about 11 for use in the extraction step by the use of any convenient food grade acid, usually hydrochloric acid or phosphoric acid, or food grade alkali, usually sodium hydroxide, as required.

The concentration of the pulse protein source in water during the extraction step may be less than 50% w/v, preferably between 5 and 25% w/v, more preferably between 5 and 15% w/v.

As in the case of the first aspect of the invention, the protein extraction step with water has the additional effect of solubilizing fats which may be present in the pulse protein source, which then results in the fats being present in the aqueous phase.

As in the case of the first aspect of the invention, the water used for the extraction step may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of any phenolics in the protein solution.

As in the case of the first aspect of the invention, the water used for the extraction step may contain an anti-foamer, such as any suitable food-grade, non-silicone based anti-foamer, to reduce the volume of foam formed upon further processing. The quantity of anti-foamer employed is generally greater than about 0.0003% w/v.

The extraction slurry is then processed to separate the aqueous protein solution from the bulk of the other components of the slurry, in any convenient manner, such as by employing a decanter centrifuge or any suitable sieve and to result in an aqueous protein solution.

The aqueous protein solution generally has a protein concentration of less than about 250 g/L, preferably about 5 to about 100 g/L, more preferably about 5 to about 50 g/L.

Calcium salt, preferably in the form of an aqueous calcium chloride solution, is added to the aqueous protein solution to precipitate mainly calcium phytate. This addition of calcium salt also may have the effect of precipitating some protein that was water soluble but not soluble in the presence of the calcium salt. Alternatively to the use of calcium salts, other alkaline earth metal compounds may be used, such as magnesium salts. The calcium salt is typically added at the pH of the protein solution arising from the initial separation step. If desired, the pH of the protein solution may be adjusted to about 4.5 to about 11, preferably about 5 to about 7 by the addition of any convenient food grade acid or food grade alkali as required prior to the addition of the calcium salt.

The calcium salt or aqueous calcium salt solution is added to the protein solution in such a manner that after calcium addition, the resulting solution has a calcium salt concentration of less than about 1.0 M, more preferably between about 0.05 M and about 0.15 M.

After calcium addition the sample is mixed by any convenient means for a period of up to about 60 minutes, preferably about 15 to about 30 minutes at a temperature of about 1° to about 100° C., preferably about 15° to about 65° C., more preferably about 20° to about 35° C.

The resulting mixture then is separated into a solids phase, which comprises the precipitated materials and fine solids not previously separated, and an aqueous phase, such as by the use of a disc stack centrifuge. This second separation step may be conducted at any temperature within the range of about 1° to about 100° C., preferably about 15° to about 65° C., more preferably about 20° to about 35° C.

Alternatively, prior to the second separation step the calcium treated aqueous pulse protein solution may be diluted with about 0.1 to about 10 volumes, preferably about 0.5 to about 2 volumes of aqueous diluent. Such dilution is usually effected using water, although dilute salt solution, such as sodium chloride or calcium chloride, having a conductivity up to about 3 mS, may be used. The optionally diluted mixture then is adjusted in pH to a value of about 1.5 to about 4.4, preferably about 2 to about 4, by the addition of any suitable food grade acid, such as hydrochloric acid or phosphoric acid. The acidified aqueous pulse protein solution then may be separated from the solids phase such as by using a disc stack centrifuge. This second separation step may be conducted at any temperature within the range of about 1° to about 100° C., preferably about 15° to about 65° C., more preferably about 20° to about 35° C.

In accordance with each of the aspects of the present invention, the solids phase may be washed with about 1 to about 20, preferably about 1 to about 10 volumes, of water to remove residual extracted pulse protein solution and contaminants and then optionally dried by any convenient means to provide a pulse protein product having a protein content of at least about 50 wt % (N×6.25) d.b., preferably a pulse protein product having a protein content of at least about 60 wt % (N×6.25) d.b., more preferably a pulse protein concentrate having a protein content of at least about 65 wt % (N×6.25) d.b.

The washing step in each of the aspects of invention may be effected using acidified water, preferably having a pH of about 4.2 to about 4.8, to reduce the phytic acid concentration of the pulse protein product. The washing step may be repeated using the same parameters to further reduce the phytic acid concentration.

The aqueous protein solution resulting from the clarification step may be subjected to the further processing steps described in the aforementioned U.S. patent applications Ser. Nos. 13/103,528, 13/289,264 and 13/556,357 to form the novel pulse protein product described in those applications.

EXAMPLES

Example 1

This Example effects extraction of pea protein using water and illustrates processing the aqueous pea protein solution.

'a' kg of yellow 'b' was added to 'c' L water at 'd' and agitated for 'e' minutes to provide an aqueous protein solution. A portion of the suspended solids were removed by centrifugation using a decanter centrifuge to produce 'f' L of protein solution having a protein content of 'g' % by weight. To 'h' L of this protein solution was added 'i' kg of a calcium chloride stock solution prepared by dissolving 'j' kg calcium chloride pellets (95.5%) in 'k' L of reverse osmosis (RO) purified water. The solution was mixed 'l', warmed to 'm'° C. and then 'n' L of 'o' at 'p' ° C. added then the 'q' L of solution centrifuged with a disc stack centrifuge. 'r' kg of watery solids discharge was collected from the disc stack centrifuge having a protein content of 's' % (N×6.25) d.b. A 't' kg portion of these solids was mixed with 'u' L of RO water 'v' then run again through the disc stack centrifuge. 'w' kg of watery solids discharge was collected after the water wash step having a protein content of 'x' % (N×6.25) d.b. A second wash step was performed by combining 'y' kg of washed solids with 'z' L of RO water and adjusting the pH to 'aa', mixing for 'ab' minutes then passing the mixture again through the disc stack centrifuge. 'ac' kg of watery, twice-washed solids discharge was collected having a protein content of 'ad' % (N×6.25) d.b. After the washing steps 'ae' kg of washed solids discharge was combined with 'af' L of RO water and that mixture pasteurized at about 'ag'° C. for 'ah'. An 'ai' kg aliquot of the pasteurized suspension was mixed with 'aj' L of RO water and spray dried to provide a product having a protein content of 'ak' % (N×6.25) d.b. The products were given the code 'al'. The designation YP711 was added to the code if the product was spray dried.

The various parameters for the preparation of the pulse protein product are given in Table 1 below:

TABLE 1

| | Parameters for the preparation of pea protein product with initial water extraction | | | | | |
|---|---|---|---|---|---|---|
| al | YP09-G19-12A | YP10-H22-12A YP711 | YP16-I11-12A YP711 | YP16-I19-12A | YP16-I25-12A | YP23-H14-13A YP711 |
| a | 24 | 56 | 26.4 | 26.4 | 35.2 | 24 |
| b | split pea flour | split pea flour | split pea flour | split pea flour | split pea flour | pea protein concentrate (dry processed) |
| c | 150 | 350 | 150 | 150 | 200 | 400 |
| d | ambient temperature | ambient temperature | ambient temperature | ambient temperature | ambient temperature | ambient temperature |
| e | 30 | 30 | 30 | 60 | 60 | 10 |
| f | Not recorded | Not recorded | 150 | 142 | 180 | Not recorded |
| g | 3.28 | 3.14 | 3.24 | 3.09 | 3.08 | 2.92 |
| h | Not recorded | Not recorded | 150 | 142 | 180 | Not recorded |
| i | 6.12 | 16.64 | 3.46 | 61.02 | 75.80 | 56 |
| j | 3 | 10 | 4 | 3.02 | 3.8 | 6 |
| k | 6 | 20 | 8 | 58 | 72 | 54 |
| l | for 15 minutes | for 15 minutes | for 15 minutes | for 15 minutes | for 15 minutes | N/A |
| m | 60 | 50 | 50 | 50 | 50 | N/A |
| n | N/A | N/A | 160 | N/A | N/A | N/A |
| o | N/A | N/A | 0.015M CaCl$_2$ | N/A | N/A | N/A |
| p | N/A | N/A | 50 | N/A | N/A | N/A |

TABLE 1-continued

Parameters for the preparation of pea protein product with initial water extraction

| | | | | | | |
|---|---|---|---|---|---|---|
| q | Not recorded | 342.1 | 316 | 200 | 257 | Not recorded |
| r | 17.62 | 41.12 | 20.88 | 20.94 | 21.66 | 44.42 |
| s | 68.2 | 61.6 | 77.8 | 61.0 | 62.7 | 73.2 |
| t | 16.92 | 41.12 | 20.88 | N/A | N/A | 44.42 |
| u | 135.36 | 329 | 167 | N/A | N/A | 355 |
| v | for 10 minutes | N/A | N/A | N/A | N/A | N/A |
| w | 20.82 | 40.74 | 19.82 | N/A | N/A | 41.74 |
| x | 78.0 | 74.9 | 88.2 | N/A | N/A | 81.8 |
| y | 20.82 | 40.74 | 19.82 | N/A | N/A | N/A |
| z | 166 | 122 | 59.46 | N/A | N/A | N/A |
| aa | N/A | 4.58 with HCl | 4.46 with HCl | N/A | N/A | N/A |
| ab | 15 minutes | 30 minutes | 30 minutes | N/A | N/A | N/A |
| ac | 13.74 | 24.7 | 17.5 | N/A | N/A | N/A |
| ad | 83.1 | 82.1 | 88.3 | N/A | N/A | N/A |
| ae | N/A | Not recorded | Not recorded | N/A | N/A | 41.74 |
| of | N/A | 0 | Not recorded | N/A | N/A | 13.79 |
| ag | N/A | 60 | 60 | N/A | N/A | 60 |
| ab | N/A | 1 minute | 2 minutes | N/A | N/A | 5 minutes |
| ai | N/A | 24.68 | Not recorded | N/A | N/A | 53.16 |
| aj | N/A | 8.48 | Not recorded | N/A | N/A | 0 |
| ak | N/A | 74.12 | 82.12 | N/A | N/A | 76.84 |

N/A = not applicable

Example 2

This Example effects extraction of pea protein using calcium chloride solution and illustrates processing the aqueous pea protein solution.

'a' kg of yellow 'b' was added to 'c' L of 'd' at 'e' and agitated for 'f' minutes to provide an aqueous protein solution. 'g' kg of calcium chloride pellets (95.5.%) was then added and the sample stirred for an additional 'h' minutes. A portion of the suspended solids were removed by centrifugation using a decanter centrifuge to produce 'i' L of protein solution having a protein content of 'j' % by weight. The protein solution was 'k' then 'l' L of 'm' at 'n' was added and the solution centrifuged using a disc stack centrifuge. 'o' kg of watery solids discharge was collected from the disc stack centrifuge having a protein content of 'p' % (N×6.25) d.b. A 'q' kg portion of these solids was mixed with 'r' L of RO water 's' then run again through the disc stack centrifuge. 't' kg of watery solids discharge was collected after the water wash step having a protein content of 'u' (N×6.25) d.b. A second wash step was performed by combining 'v' kg of washed solids with 'w' L of RO water and adjusting the pH to 4.5 with HCl solution, mixing for 30 minutes then passing the mixture again through the disc stack centrifuge. 'x' kg of watery, twice-washed solids discharge was collected having a protein content of 'y' % (N×6.25) d.b. After the washing steps 'z' kg of washed solids discharge was combined with 'aa' L of RO water and the mixture pasteurized at about 'ab'° C. for 'ac' minutes. An 'ad' kg aliquot of the suspension was spray dried to provide a product having a protein content of 'ae' % (N×6.25) d.b. The products were given the code 'af'. The designation YP711 was added to the code if the product was spray dried.

The parameters for the preparation of the pea protein product are set forth in Table 2 below:

TABLE 2

Parameters for the preparation of pea protein product with initial saline extraction

| | | | | | | |
|---|---|---|---|---|---|---|
| af | YP09-G31-12A YP711 | YP11-H02-12A | YP11-I20-12A | YP11-I27-12A | YP11-J15-12A | YP20-G03-13A YP711 |
| a | 48 | 15 | 11.25 | 15 | 15 | 30 |
| b | split pea flour | pea protein concentrate (dry processed) | pea protein concentrate (dry processed) | pea protein concentrate (dry processed) | pea protein concentrate (dry processed) | pea protein concentrate (dry processed) |
| c | 300 | 150 | 150 | 200 | 150 | 300 |
| d | RO water | 0.13M CaCl$_2$ solution | 0.13M CaCl$_2$ solution | 0.13M CaCl$_2$ solution | 0.15M CaCl$_2$ solution | 0.08M CaCl$_2$ solution |
| e | ambient temperature | ambient temperature | ambient temperature | ambient temperature | ambient temperature | ambient temperature |
| f | 30 | 30 | 15 | 15 | 15 | 30 |
| g | 5.68 | N/A | N/A | N/A | N/A | N/A |
| h | 15 | N/A | N/A | N/A | N/A | N/A |
| i | 284 | 148 | Not recorded | 234.8 | Not recorded | 258 |
| j | 2.77 | 4.36 | 3.14 | 2.82 | 4.03 | 3.83 |
| k | N/A | N/A | warmed to 50° C. | warmed to 50° C. | warmed to 50° C. | N/A |
| l | N/A | N/A | N/A | N/A | 163 | N/A |
| m | N/A | N/A | N/A | N/A | RO water | N/A |
| n | N/A | N/A | N/A | N/A | 50° C. | N/A |

TABLE 2-continued

Parameters for the preparation of pea protein product with initial saline extraction

| | | | | | | |
|---|---|---|---|---|---|---|
| o | 26.08 | 16.16 | 13.94 | 12.42 | 19.42 | 24.56 |
| p | 61.1 | 66.2 | 61.1 | 64.9 | 70.4 | 77.7 |
| q | 26.08 | N/A | N/A | N/A | N/A | 24.5 |
| r | 208.6 | N/A | N/A | N/A | N/A | 196 |
| s | for 20 minutes | N/A | N/A | N/A | N/A | N/A |
| t | 20.28 | N/A | N/A | N/A | N/A | 15.74 |
| u | 77.8 | N/A | N/A | N/A | N/A | 95.5 |
| v | 10.14 | N/A | N/A | N/A | N/A | N/A |
| w | 30.42 | N/A | N/A | N/A | N/A | N/A |
| x | 10.48 | N/A | N/A | N/A | N/A | N/A |
| y | 81.3 | N/A | N/A | N/A | N/A | N/A |
| z | 10.48 | N/A | N/A | N/A | N/A | 15.74 |
| aa | 5 | N/A | N/A | N/A | N/A | 14.28 |
| ab | N/A | N/A | N/A | N/A | N/A | 65 |
| ac | N/A | N/A | N/A | N/A | N/A | 10 |
| ad | 15.48 | N/A | N/A | N/A | N/A | 29.18 |
| ae | 73.42 | N/A | N/A | N/A | N/A | 74.17 |

N/A = not applicable

Example 3

This Example illustrates the phytic acid content of the spray dried yellow pea protein products prepared as described in Examples 1 and 2.

Samples were tested for phytic acid content by the method of Latta and Eskin (J. Agric. Food Chem., 28: 1313-1315). The phytic acid values determined are shown in Table 3 below.

TABLE 3

Phytic acid content of spray dried washed solids samples

| sample | % phytic acid d.b. |
|---|---|
| YP09-G31-12A YP711* | 4.22 |
| YP10-H22-12A YP711* | 4.32 |
| YP16-I11-12A YP711* | 3.16 |
| YP20-G03-13A YP711 | 5.77 |
| YP23-H14-13A YP711 | 4.92 |

*samples prepared with second wash step utilizing water at about pH 4.5

As may be seen from the results in Table 3, samples prepared with a second wash step with water at about pH 4.5 had somewhat lower phytic acid content than samples prepared without the lower pH water wash step.

The effect of this second wash step on the phytic acid content is seen more clearly when looking specifically at batch YP09-G31-12A. A sample of solids washed once with water at natural pH was spray dried as well as the sample washed a second time with water at pH 4.5. The protein and phytic acid values determined for these dry samples are shown in Table 4.

TABLE 4

Protein and phytic acid content of spray dried washed solids samples

| sample | % protein (N × 6.25) d.b. | % phytic acid d.b. |
|---|---|---|
| washed once with water | 69.96 | 7.32 |
| washed a second time with water at pH 4.5 | 73.42 | 4.22 |

As may be seen from the results in Table 4, the second wash step with water at pH 4.5 lowered the phytic acid content of the product without lowering the protein content.

Example 4

This Example contains an evaluation of the crude fibre content of some of the spray dried yellow pea protein products produced by the methods of Examples 1 and 2. Crude fibre levels were determined according to AOCS Procedure Ba 6a-05.

The crude fibre results are shown in Table 5.

TABLE 5

Crude fibre content of spray dried washed solids samples

| sample | % crude fibre d.b. |
|---|---|
| YP09-G31-12A YP711 | 0.78 |
| YP10-H22-12A YP711 | 0.34 |
| YP23-H14-13A YP711 | 0.00 |

As may be seen from the results presented in Table 5, all samples tested were low in crude fibre content.

Example 5

This Example contains an evaluation of the solubility in water of some of the spray dried yellow pea protein products produced by the methods of Examples 1 and 2. Solubility was tested based on protein solubility (termed protein method, a modified version of the procedure of Morr et al., J. Food Sci. 50:1715-1718) and total product solubility (termed pellet method).

Sufficient protein powder to supply 0.5 g of protein was weighed into a beaker and wetted by mixing with about 20-25 ml of reverse osmosis (RO) purified water. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with diluted NaOH or HCl. A sample was also prepared at natural pH. For the pH adjusted samples, the pH was measured and corrected periodically during the 60 minutes stirring. After the 60 minutes of stirring, the samples were made up to 50 ml total volume with RO water, yielding a 1% w/v protein dispersion. The protein content of the dispersions was determined by combustion analysis using a Leco Nitrogen Determinator. Aliquots (20 ml) of the dispersions were then transferred to pre-weighed centrifuge tubes that had been dried overnight in a 100° C. oven then cooled in a desiccator and the tubes capped. The samples were centrifuged at 7,800 g for 10 minutes, which sedimented insoluble material and yielded a supernatant. The protein content of the supernatant was measured by combustion analysis and then the supernatant and the tube lids were discarded and the pellet material dried overnight in an oven set at 100° C. The next morning the tubes were transferred to a desiccator and allowed to cool. The weight of dry pellet material was recorded. The dry weight of the initial protein powder was calculated by multiplying the weight of powder used by a factor of ((100-moisture content of the powder (%))/100). Solubility of the product was then calculated two different ways:

Solubility (protein method) (%)=(% protein in supernatant/% protein in initial dispersion)×100    1)

Solubility (pellet method) (%)=(1−(weight dry insoluble pellet material/((weight of 20 ml of dispersion/weight of 50 ml of dispersion)×initial weight dry protein powder)))×100    2)

Values calculated as greater than 100% were reported as 100%.

The natural pH values of the 1% w/v protein solutions of the protein products are shown in Table 6:

TABLE 6

Natural pH of solutions prepared in water at 1% protein

| Batch | Product | Natural pH |
|---|---|---|
| YP09-G31-12A | YP711 | 5.02 |
| YP10-H22-12A | YP711 | 5.14 |
| YP20-G03-13A | YP711 | 5.68 |
| YP23-H14-13A | YP711 | 5.60 |

The solubility results obtained are set forth in the following Tables 7 and 8:

TABLE 7

Solubility of products at different pH values based on protein method

| | | Solubility (protein method) (%) | | | | | | |
|---|---|---|---|---|---|---|---|---|
| Batch | Product | pH 2 | pH 3 | pH 4 | pH 5 | pH 6 | pH 7 | Nat. pH |
| YP09-G31-12A | YP711 | 13.5 | 1.0 | 4.7 | 0.0 | 1.9 | 44.6 | 0.0 |
| YP10-H22-12A | YP711 | 15.6 | 1.4 | 2.4 | 4.9 | 7.5 | 30.5 | 1.8 |
| YP20-G03-13A | YP711 | 22.3 | 1.8 | 1.8 | 4.5 | 3.0 | 19.7 | 0.5 |
| YP23-H14-13A | YP711 | 19.5 | 6.1 | 10.9 | 5.8 | 7.0 | 7.1 | 7.4 |

TABLE 8

Solubility of products at different pH values based on pellet method

| | | Solubility (pellet method) (%) | | | | | | |
|---|---|---|---|---|---|---|---|---|
| Batch | Product | pH 2 | pH 3 | pH 4 | pH 5 | pH 6 | pH 7 | Nat. pH |
| YP09-G31-12A | YP711 | 11.4 | 8.2 | 10.3 | 9.3 | 7.6 | 34.5 | 9.1 |
| YP10-H22-12A | YP711 | 14.8 | 10.1 | 10.7 | 12.1 | 8.8 | 19.5 | 10.3 |
| YP20-G03-13A | YP711 | 20.6 | 12.7 | 13.7 | 11.4 | 9.6 | 15.8 | 10.7 |
| YP23-H14-13A | YP711 | 30.0 | 15.7 | 17.1 | 14.1 | 13.7 | 16.6 | 12.7 |

As can be seen from the results presented in Tables 7 and 8, the solubility values were generally low across the entire pH range, regardless of which solubility determination method was used.

Example 6

This Example illustrates the water binding capacity of the spray dried yellow pea protein products prepared by the methods of Examples 1 and 2.

The water binding capacity of the products was determined by the following procedure. Protein powder (1 g) was weighed into centrifuge tubes (50 ml) of known weight. To this powder was added approximately 20 ml of reverse osmosis purified (RO) water at the natural pH. The contents of the tubes were mixed using a vortex mixer at moderate speed for 1 minute. The samples were incubated at room temperature for 5 minutes then mixed with the vortex for 30 seconds. This was followed by incubation at room temperature for another 5 minutes then another 30 seconds of vortex mixing. The samples were then centrifuged at 1,000 g for 15 minutes at 20° C. After centrifugation, the supernatant was carefully poured off, ensuring that all solid material remained in the tube. The centrifuge tube was then re-weighed and the weight of water saturated sample was determined.

Water binding capacity (WBC) was calculated as:

WBC (ml/g)=(mass of water saturated sample (g)−mass of initial sample (g))/(mass of initial sample (g)×total solids content of sample)

The water binding capacity results are shown in Table 9.

TABLE 9

Water binding capacity of pea protein products

| sample | water binding capacity (ml/g) |
|---|---|
| YP09-G31-12A YP711 | 1.51 |
| YP10-H22-12A YP711 | 1.57 |
| YP16-I11-12A YP711 | 1.97 |
| YP20-G03-13A YP711 | 1.66 |
| YP23-H14-13A YP711 | 1.52 |

As may be seen from the results in Table 9, the pea protein products all had a low to moderate water binding capacity.

Example 7

This Example illustrates the oil binding capacity of the spray dried yellow pea protein products prepared by the methods of Examples 1 and 2.

The oil binding capacity of the products was determined by the following procedure. Protein powder (1 g) was weighed into centrifuge tubes (50 ml) of known weight. To this powder was added approximately 20 ml of canola oil (Canada Safeway, Calgary, AB). The contents of the tubes were mixed using a vortex mixer at moderate speed for 1 minute. The samples were incubated at room temperature for 5 minutes then mixed with the vortex for 30 seconds. This was followed by incubation at room temperature for another 5 minutes then another 30 seconds of vortex mixing. The samples were then centrifuged at 1,000 g for 15 minutes at 20° C. After centrifugation, the supernatant was carefully poured off, ensuring that all solid material remained in the tube. The centrifuge tube was then re-weighed and the weight of oil saturated sample was determined.

Oil binding capacity (OBC) was calculated as:

OBC (ml/g)=((mass of oil saturated sample (g)−mass of initial sample (g))/0.914 g/ml)/(mass of initial sample (g)×total solids content of sample)

The oil binding capacity results are shown in Table 10.

TABLE 10

Oil binding capacity of pea protein products

| sample | oil binding capacity (ml/g) |
| --- | --- |
| YP09-G31-12A YP711 | 1.24 |
| YP10-H22-12A YP711 | 1.36 |
| YP16-I11-12A YP711 | 1.58 |
| YP20-G03-13A YP711 | 1.34 |
| YP23-H14-13A YP711 | 1.07 |

As may be seen from the results in Table 10, the pea protein products all had a low to moderate oil binding capacity.

Example 8

This Example effects extraction of lentil protein using calcium chloride solution and illustrates processing the aqueous lentil protein solution.

'a' kg of 'b' was added to 'c' L of 0.13M $CaCl_2$ at ambient temperature and agitated for 30 minutes to provide an aqueous protein solution. A portion of the suspended solids were removed by centrifugation using a decanter centrifuge to produce 'd' L of protein solution having a protein content of 'e' % by weight. The protein solution was then centrifuged using a disc stack centrifuge. 'f' kg of watery solids discharge was collected from the disc stack centrifuge having a protein content of 'g' % (N×6.25) d.b. The product was given the code 'h'. The parameters employed are set forth in Table 11 below.

TABLE 11

Parameters for the preparation of lentil protein product with initial saline extraction

| h | LE02-J23-13A | LE01-J24-13A |
| --- | --- | --- |
| a | 20 | 20 |
| b | red split lentil flour | green whole lentil flour |
| c | 200 | 200 |
| d | not recorded | not recorded |
| e | 1.91 | 1.82 |
| f | 20.92 | not recorded |
| g | 51.6 | 53.4 |

SUMMARY OF THE DISCLOSURE

In summary of this disclosure, a pulse protein product, preferably a pulse protein concentrate, is produced as a by-product from the clarification of pulse protein extract solution. Modifications are possible within the scope of the invention.

What we claim is:

1. A method of forming a pulse protein product having a protein content of at least about 50 wt % (N×6.25) d.b., which comprises:
    (a) mixing a pulse protein source with water to form a slurry,
    (b) separating the aqueous pulse protein solution from the bulk of the other components of the slurry,
    (c) adding a calcium salt to the aqueous pulse protein solution to precipitate calcium phytate,
    (d) applying a second separation step to the calcium treated pulse protein solution to recover the precipitate as well as any finer solids not removed in the initial separation step (b), and
    (e) washing the solid materials recovered in the second separation step to remove impurities and provide washed solid materials, and
    (f) drying the washed solid materials to provide the pulse protein product.

2. The method of claim 1 wherein the water extraction step is effected for about 1 to about 60 minutes at a temperature of about 1° to about 70° C.

3. The method of claim 1 wherein the water extraction is carried out at a pH of about 4.5 to about 11.

4. The method of claim 1 wherein the aqueous pulse protein solution has a protein concentration of less than 250 g/L.

5. The method of claim 1 wherein the calcium salt is added in the form of an aqueous calcium salt solution.

6. The method of claim 1 wherein the calcium salt is added in an amount to provide a calcium treated solution having a calcium salt concentration of less than about 1.0 M.

7. The method of claim 6 wherein the calcium treated protein solution is mixed for up to about 60 minutes at a temperature of about 1° to about 100° C.

8. The method of claim 1 wherein the solids recovered in the second separation step are washed in at least one washing step with between about 1 and about 20 volumes of water.

9. The method of claim 8 wherein said at least one washing step is effected using acidified water.

10. The method of claim 9 wherein the acidified water has a pH of about 4.2 to about 4.8.

11. The method of claim 1 wherein the pulse protein product has a protein concentration of at least about 60 wt % (N×6.25) d.b.

12. The method of claim 11 wherein said pulse protein product has a protein concentration of at least about 65 wt % (N×6.25) d.b.

13. A pulse protein product having a protein content of at least about 50 wt % (N×6.25) d.b. wherein the natural pH value of a 1% w/v protein solution is between 5.02 and 5.68 and having each of the following parameters:
    (a) a phytic acid content of at least 2.5 wt % d.b.,
    (b) a crude fibre content of less than about 1.5 wt % d.b.,
    (c) a solubility of less than about 15 wt % over a pH range of about 3 to about 6
    when solubility is determined by the relationship: Solubility (%)=(% protein in supernatant/% protein in initial dispersion)×100, (d) a solubility of less than about 25 wt % over a pH range of about 3 to about 6 when solubility is determined by the relationship: Solubility (%)=(1−(weight dry insoluble pellet material/((weight of 20 ml of dispersion/weight of 50 ml of dispersion)×initial weight dry protein powder)))×100, (e) a water binding capacity of less than about 2.5 ml/g, and (f) an oil binding capacity of less than about 2 ml/g.

14. The pulse protein product of claim 13 having a protein content of at least 60 wt %.

15. The pulse protein product of claim 13 which is a concentrate having a protein content of at least about 65 wt %.

* * * * *